(12) United States Patent
Herb et al.

(10) Patent No.: US 11,504,954 B2
(45) Date of Patent: Nov. 22, 2022

(54) FILM COMPOSITE FOR PACKAGING TRANSDERMAL PATCHES, AND PACKAGE MADE OF SUCH A FILM COMPOSITE

(71) Applicant: Huhtamaki Flexible Packaging Germany GmbH & Co. KG, Ronsberg (DE)

(72) Inventors: Manuella Herb, Görisried (DE); Michael Dorn, Dietmannsried (DE); Thomas Stroh, Memmingen (DE)

(73) Assignee: Huhtamaki Flexible Packaging Germany GmbH & Co. KG, Ronsberg (DE)

( * ) Notice: Subject to any disclaimer, the term of this patent is extended or adjusted under 35 U.S.C. 154(b) by 18 days.

(21) Appl. No.: 16/516,792

(22) Filed: Jul. 19, 2019

(65) Prior Publication Data

US 2020/0031107 A1    Jan. 30, 2020

(30) Foreign Application Priority Data

Jul. 24, 2018   (DE) .................... 10 2018 212 303.9
Oct. 11, 2018   (DE) .................... 10 2018 125 195.5

(51) Int. Cl.
*B32B 27/32*   (2006.01)
*A61K 9/70*    (2006.01)
(Continued)

(52) U.S. Cl.
CPC .......... *B32B 27/327* (2013.01); *A61K 9/7023* (2013.01); *B32B 7/10* (2013.01);
(Continued)

(58) Field of Classification Search
CPC ....... B32B 27/327; B32B 27/325; B32B 7/10; B32B 15/16; B32B 2250/04; B32B 2556/00; A61K 9/7023
See application file for complete search history.

(56) References Cited

U.S. PATENT DOCUMENTS

2005/0181154 A1*   8/2005   Toft ........................ C08L 23/08
                                                        428/34.2
2007/0160789 A1    7/2007   Merical et al.
(Continued)

FOREIGN PATENT DOCUMENTS

WO    2017114922 A1    7/2017

OTHER PUBLICATIONS

German Search Report for corresponding DE 10 2018 125 195.5 dated Feb. 25, 2019, 10 pgs.
(Continued)

*Primary Examiner* — Hong Yu
(74) *Attorney, Agent, or Firm* — Rankin, Hill & Clark LLP (57) ABSTRACT a film composite for manufacturing a package for planar carriers of pharmaceutical active substances, for example transdermal patches, encompassing, in a direction from the outer side of the film composite toward its inner side: a metal layer; an acrylic-acid-containing joining layer; a polyethylene layer; and a COC layer made of cycloolefin copolymer, a side of the COC layer which faces away from the metal layer being an exposed surface of the film composite, wherein provision is made that the polyethylene layer encompasses metallocene polyethylene.

29 Claims, 3 Drawing Sheets

(51) Int. Cl.
*B32B 15/16* (2006.01)
*B32B 7/10* (2006.01)

(52) U.S. Cl.
CPC ............ *B32B 15/16* (2013.01); *B32B 27/325* (2013.01); *B32B 2250/04* (2013.01); *B32B 2556/00* (2013.01)

(56) References Cited

U.S. PATENT DOCUMENTS

| 2015/0225151 A1 | 8/2015 | Osborn et al. |
| 2017/0136747 A1* | 5/2017 | Torradas ................. B32B 27/08 |
| 2018/0354702 A1 | 12/2018 | Liu et al. |

OTHER PUBLICATIONS

European Search Report for corresponding EP 19 18 6607 dated Dec. 5, 2019, 6 pgs.

* cited by examiner

FILM COMPOSITE FOR PACKAGING TRANSDERMAL PATCHES, AND PACKAGE MADE OF SUCH A FILM COMPOSITE

The present invention relates to a film composite for manufacturing a package for planar carriers of pharmaceutical active substances, for example transdermal patches, encompassing, in a direction from the designated outer side of the film composite toward its designated inner side: a metal layer; an acrylic-acid-containing joining layer; a polyethylene layer; and a COC layer made of cycloolefin copolymer, a side of the COC layer which faces away from the metal layer being an exposed surface of the film composite.

BACKGROUND OF THE INVENTION

A film composite of this kind, for the aforesaid purpose of manufacturing a package for pharmaceutical active-substance carriers, is known from WO 2015/123211 A1. The film composite of the species comes into direct contact with the planar carrier of a pharmaceutical active substance, and thus with the pharmaceutical active substance itself. The relevant pharmaceutical active substances are active substances such as nicotine, fentanyl, or lidocaine. The stress on the film composite produced by these pharmaceutical active substances is considerable. It is necessary to ensure in this context on the one hand that the film composite survives as such over the long term in order to prevent undesired release of the pharmaceutical active substance of the active-substance carrier. Even if the film composite survives, i.e., does not at least locally delaminate, for example, under the influence of the pharmaceutical active substance diffusing into composite layers, it is necessary on the other hand to ensure that the pharmaceutical active substance cannot diffuse or migrate through the film composite.

In order to increase the diffusion barrier effect of the film composite with respect to the pharmaceutical active substances packaged by it, it is known to select the proportion of cycloolefin copolymer (COC) in the COC layer that is innermost in the subsequent package to be as high as possible. As the COC concentration in the COC layer rises, however, it becomes increasingly difficult to maintain the stability of the film composite, for example to prevent delamination or similar disintegration phenomena.

WO 2017/114922 A1 also discloses film composites for creating packages for planar pharmaceutical active substance carriers.

SUMMARY OF THE INVENTION

An object of the present invention is therefore to embody the film composite recited initially with the greatest possible chemical and mechanical stability with regard to the pharmaceutical active substances that are to be packaged, in light of its purpose of constituting a safe, including childproof, package for planar pharmaceutical active-substance carriers.

This object is achieved according to the present invention by a film composite of the kind recited initially in which the polyethylene layer encompasses metallocene polyethylene. The reason is that experiments have shown that given otherwise identical dimensions for the film composite, adhesion of the COC layer to the polyethylene layer is considerably better when the polyethylene layer encompasses metallocene polyethylene. "Metallocene polyethylene" in this context is polyethylene that has been manufactured in known fashion using metallocene catalysts.

The higher the COC concentration in the COC layer, the greater the gain in adhesion, in terms of the adhesive effect between the COC layer and the polyethylene layer, which is achievable by the use of metallocene polyethylene as compared with conventional polyethylene. Because the COC layer comprises a COC proportion that is as high as possible (at least 95 wt %, preferably at least 99.8 wt %, of the mass of the COC as a whole) in order to achieve a maximum barrier effect with respect to pharmaceutical active substances that are stored in the planar active-substance carrier, a particularly significant adhesion advantage can be achieved with the utilization, as presented here, of metallocene polyethylene in the polyethylene layer arranged between the acrylic-acid-containing joining layer and the COC layer.

In doubtful cases, for example if more than one polymer layer of the film composite contains COC, a COC layer is to be considered a "COC layer" for purposes of the present Application only if it contains at least 50 wt % COC in terms of its layer mass. The aforesaid polyethylene layer that contains metallocene polyethylene is preferably devoid of COC.

In principle, an improvement in the adhesion of the COC layer to the polyethylene layer can already be achieved with comparatively small quantities of metallocene polyethylene. In a context of comparative samples of different film-composite sheets that are otherwise dimensionally identical, the improvement in the adhesive effect is particularly large if the proportion of metallocene polyethylene in terms of the total polyethylene of the polyethylene layer is at least 50 wt %. It is therefore also possible in principle to use so-called polyethylene blends, in which metallocene polyethylene is blended with non-metallocene polyethylene, to constitute the polyethylene layer.

Because of the advantageous adhesion-enhancing effect of metallocene polyethylene, the proportion thereof (always in percent by weight) in terms of the total polyethylene contained in the polyethylene layer is preferably as high as possible, preferably higher than 90 wt %, particularly preferably higher than 96 wt %.

It has proven to be advantageous, in order to enhance the adhesion effect and also the processability of the film composite on corresponding processing machines to produce packages constituted therefrom, if the polyethylene layer encompasses a metallocene LLDPE. The polyethylene layer preferably encompasses only metallocene LLDPE as the metallocene polyethylene.

In order to achieve good running properties for a film-composite web in the aforementioned processing machines, the density of the metallocene polyethylene is advantageously in a range between 0.917 and 0.921 g/m². In order to achieve permanent sealed seams with high strength and high density, the metallocene polyethylene additionally or alternatively has a melt flow index (melt flow rate, MFR) of between 6 and 10 g/10 min., measured per ISO 1133 at a test temperature of 190° C. and using a test element having a weight of 2.16 kg. This is because in addition to the COC, constituting the external barrier layer and sealing layer, the polyethylene layer can contribute to sealed join of the film composite.

Any type of metallocene polyethylene in the polyethylene layer provides a desired enhancement of the adhesion effect of the COC layer on the polyethylene layer, compared with a polyethylene layer of the same dimensions and/or the same weight per unit area in the film composite. In addition, however, the rigidity of the polyethylene layer, and thus of the film composite as a whole, can be influenced by using different types of metallocene polyethylene. Advantageous rigidity of the polyethylene layer, in a context of predefined dimensions thereof, can be obtained by the fact that the polyethylene layer encompasses a C6 metallocene polyethylene and/or a C8 metallocene polyethylene, or is made of the aforesaid types of metallocene polyethylene. According to previous experiments, for a predefined film composite and in particular for a predefined dimension and/or weight per unit area of the polyethylene layer, C8 metallocene polyethylene offers the best results in terms of achieving on the one hand layer rigidity of the polyethylene layer and on the other hand composite rigidity of the film composite.

It is understandably advantageous for that reason if the polyethylene layer encompasses only a C8 metallocene polyethylene as a metallocene polyethylene. Based on what is stated above, it is particularly preferably a C8 metallocene LLDPE.

The polyethylene layer is preferably applied using the extrusion method, particularly preferably coextruded with the COC layer.

A commercially available metallocene polyethylene that is outstandingly applicable as a polyethylene layer in the aforesaid film composite is the polyethylene obtainable from the Dow Chemical Company under the trade name "Elite™ 5811."

In order to achieve the greatest possible adhesion effect for the partial composite, made up of a polyethylene layer and COC layer, on the metal layer, the acrylic-acid-containing joining layer preferably encompasses or is made of an ethylene-acrylic acid (EAA) copolymer.

The acrylic-acid-containing joining layer is preferably also applied onto the metal layer by extrusion. Particularly preferably, a partial composite made up of an acrylic-acid-containing joining layer, in particular an EAA layer; a polyethylene layer; and a COC layer is applied onto the metal layer by coextrusion in one collective extrusion step.

The metal layer serves as an oxygen barrier and gas barrier to protect package contents from external influences, and furthermore as a barrier for pharmaceutical active substances and constituents thereof which reach the metal layer as a result of diffusion through the COC layer, the polyethylene layer, and the acrylic-acid-containing joining layer. Preferably the metal layer is an aluminum layer.

Preferably each of the layers, from among the acrylic-acid-containing joining layer, polyethylene layer, and COC layer, has a layer thickness in the range from approximately 7 µm to 15 µm. On the one hand this ensures outstanding attachment to the metal layer; on the other hand, in this thickness range not only the COC layer but also the polyethylene layer can serve to produce a sealed join to the COC layer of a film composite of similar construction. Because, in the instance recited, the polyethylene layer located below the COC layer can also contribute in particularly effective and reliable fashion to production of a sealing join, the values indicated above for the melt flow index (MFR) are highly advantageous in terms of achieving outstanding sealing properties for the film composite having the exposed COC layer. The thickness values of the three, preferably coextruded layers (acrylic-acid-containing joining layer, polyethylene layer, and COC layer) are preferably each in the range from 9 µm to 12 µm. In order to achieve outstanding sealing properties with the involvement not only of the COC layer as an external sealing layer but also the polyethylene layer located therebelow, there is preferably little difference between the layer thicknesses of the polyethylene layer and of the COC layer. In order to achieve optimum attachment of the COC layer and the polyethylene layer to the metal layer without thereby making the film composite undesirably thick, the thickness of the acrylic-acid-containing joining layer also preferably differs little from the thickness of the two layers recited above (polyethylene layer and COC layer). The thickness values of the aforesaid layers, referred to the thinnest of the aforesaid layers, preferably differ by no more than 15%, preferably by no more than 11%. A triple composite made up of an acrylic-acid-containing joining layer, a polyethylene layer, and a COC layer can then easily be coextruded, the resulting film composite then exhibiting very good running properties on processing machines for processing the film composite to yield a package, and furthermore exhibiting very good sealing properties.

In principle, the film composite can be used as it is described above. For further protection of the film composite it can have, on that side of the metal layer which faces away from the COC layer, at least one further layer made of paper and/or plastic. As a result, the metal layer is a completely internal layer of the film composite, and as such is better protected from external influences. Because the COC layer as a rule is an entirely internally located layer of a package constituted from the film composite, provision of the at least one further layer simplifies the application of product information onto the outer side of the film composite which faces toward the consumer, which information would otherwise need to be applied, with greater complexity, onto the metal layer.

The at least one further layer is preferably laminated onto the metal layer or onto a further layer already present thereon. A solvent-containing laminating adhesive having a coating weight per unit area of 2 to 4 $g/m^2$, preferably having a coating weight per unit area of 3 $g/m^2$, is preferably used for this.

For easy imprinting and for child safety of a package constituted from the film composite, in order to prevent undesired opening and exposure of the pharmaceutical active substances packaged therein, the film composite preferably comprises, on that side of the metal layer which faces away from the COC layer, both a further layer made of paper and a further layer made of plastic. Because of the particular easy imprintability of the paper layer and thus a particularly simple and inexpensive capability for equipping the film composite, and/or a package constituted therewith, with consumer information, the plastic layer is preferably located closer to the metal layer than is the paper layer. The paper layer is preferably an external layer of the film composite. A imprint printed onto the paper layer can be at least partly, or preferably completely, covered by a protective layer, for example a clear lacquer.

To protect against undesired tearing by children, the further layer made of plastic is preferably a biaxially oriented plastic.

In experiments, polyethylene terephthalate and/or polyamide have proven successful as a plastic for the at least one further plastic layer. Plastic layers made of the aforesaid plastics have sufficient mechanical and thermal stability and, especially in oriented form, provide a further barrier effect against diffusion of gases and vapors. The further plastic layer can thus, in one direction, protect the metal layer from chemical attack from outside, and in the opposite direction can additionally retain the pharmaceutical active substance, or constituents thereof, if they happen to pass through the metal layer.

When the film composite has a further layer made of paper on that side of the metal layer which faces away from the COC layer, that paper layer preferably has a thickness of 35 to 45 µm, particularly preferably 39 to 41 µm. Additionally or alternatively, the further layer made of paper can have a weight per unit area of 35 to 45 g/m$^2$, in particular 39 to 41 g/m$^2$.

When the film composite has, on that side of the metal layer which faces away from the COC layer, a further layer made of plastic, the latter layer preferably has a thickness of 19 to 27 µm, in particular 22 to 24 µm. Additionally or alternatively, the additional layer made of plastic has a weight per unit area of 28 to 36 g/m$^2$, in particular 31 to 33 g/m$^2$. These values for thickness and weight per unit area offer a very good compromise among sufficient mechanical strength, thermal stability, and low overall thickness for the film composite.

Because the above-described film composite is particularly suitable for manufacturing a package for a planar carrier of pharmaceutical active substances, for example a transdermal patch, the present invention also relates to such a package encompassing two film-composite sheets each made of a film composite as described and refined above. The film-composite sheets are arranged with mutually facing COC layers to form a carrier receiving space, and are joined to one another by local sealing of COC layer regions. Portions of the mutually facing COC layer regions are sealed to one another, preferably with participation of the polyethylene layer that has metallocene polyethylene and is located below the COC layers. The sealed seam then preferably encompasses a mixture of COC and metallocene polyethylene. The sealed seam then extends, in a thickness direction, into the polyethylene layer. Other portions of the mutually facing COC layer regions of the two film-composite sheets are located unjoinedly opposite one another. When a planar carrier of pharmaceutical active substances is received in the package, said carrier is located between respective oppositely located portions, unjoined to one another, of a COC layer of a film-composite sheet involved in the constitution of the package.

A "planar carrier of pharmaceutical active substances" is understood to be a substrate that respectively has, in its two principal directions of extent that are orthogonal to one another and to the substrate thickness direction, dimensions that are at least 10 times, preferably at least 30 times, greater than the dimension of the substrate in a thickness direction, and that is embodied to release a pharmaceutical active substance stored in the substrate.

To save space while providing durably effective shielding of the pharmaceutical active substance packaged therein, the package can be a four-side-sealed pouch having a sealed seam surrounding the carrier receiving space.

A planar active-substance carrier received in the carrier receiving space of the package as described above is preferably a transdermal patch. The pharmaceutical active substance in the active-substance carrier preferably encompasses nicotine and/or fentanyl and/or lidocaine and/or another known active substance for administration by means of a transdermal patch.

The "designated" internal or external side of the film composite refers respectively to that side of the film composite which respective constitutes, on a package subsequently constituted from the film composite, a portion of the inner side or the outer side of the package.

The film composite preferably comprises only the layers recited in the present Application.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which form a part hereof and wherein.

DESCRIPTION OF PREFERRED EMBODIMENTS

Figure 1:
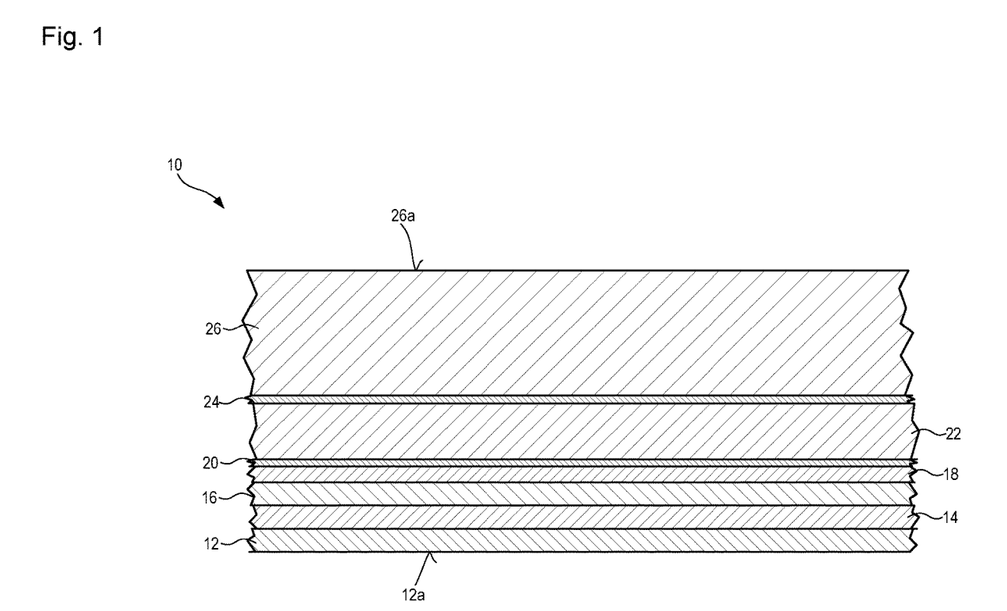
FIG. 1 is a cross-sectional view through an embodiment according to the present invention of a film composite of the present Application.

Referring now to the drawings wherein the showings are for the purpose of illustrating preferred and alternative embodiments of the invention only and not for the purpose of limiting the same, in FIG. 1, an embodiment according to the present invention of a film composite of the present Application is labeled in general with the number 10. The depiction in FIG. 1 is merely schematic. In particular, the thicknesses of the individual layers of film composite 10 are not illustrated accurately to scale. Film composite 10 has on its designated inner side a COC layer 12 that has a COC content of approximately 99.8 wt %. The proportion of COC in COC layer 12 is selected to be as high as possible in order to provide, with COC layer 12, an optimum barrier layer against migration and diffusion of pharmaceutical active substances such as nicotine and/or fentanyl and/or lidocaine. A surface 12a of COC layer 12 constitutes an exposed outer surface of film composite 10. COC layer 12 preferably has a thickness of 9.8 to 10.0 µm.

A polyethylene layer 14 is joined to COC layer 12 by coextrusion. Polyethylene layer 14 is preferably devoid of COC, and encompasses at least 50 wt % metallocene polyethylene, preferably C8 metallocene LLDPE. In the example depicted, the proportion of C8 metallocene LLDPE in terms of the total polyethylene mass of polyethylene layer 14 is more than 95 wt %. Extremely good adhesion of COC layer 12 to polyethylene layer 14, and thus good protection from delamination, are thereby achieved. The use of C8 metallocene LLDPE, as opposed to the C4 or C6 types that are also possible, results not only in good adhesion of COC layer 12 to a polyethylene layer 14 but also in a polyethylene layer 14 having advantageous rigidity properties. The melt flow index (MFR) of polyethylene layer 14 is approximately 8 g/10 min., measured per ISO 1133 at a test temperature of 190° C. using a test weight of 2.16 kg. The density of polyethylene layer 14 is preferably 0.919 g/m$^2$.

Thanks to the value selected for the melt flow index, although polyethylene layer 14 is not an external layer of film composite 10 it can participate in a sealed join of film composite 10 on COC layer 12 side. High sealing strength values, and a very high-quality sealed seam, are thereby achieved. COC layer 12 is not only a barrier layer of film composite, but also its sealable layer.

In the example depicted, the thickness of polyethylene layer 14 is between 10.8 and 11.0 µm. Polyethylene layer 14 and COC layer 12 are thus of approximately equal thickness; COC layer 12 can be slightly thinner. This balanced thickness relationship between polyethylene layer 14 and COC layer 12 also contributes to the attainment of permanently strong and diffusion-proof sealed joins.

On the side facing away from COC layer 12, polyethylene layer 14 is joined to a joining layer 16 made of an ethylene-acrylic acid (EAA) copolymer, in order to join COC layer 12 and polyethylene layer 14, by means of joining layer 16, to an aluminum layer 18.

Joining layer 16, which is between 10.6 and 10.8 µm thick in the example depicted, has been coextruded together with polyethylene layer 14 and COC layer 12, and applied onto aluminum layer 18 in the course of coextrusion.

Aluminum layer 18, which serves as a further barrier layer, is 8 to 10 µm thick, preferably 9 µm thick, in the example depicted.

A film composite made up of layers 12, 14, 16, and 18 is already a stable composite that is outstandingly suitable for manufacturing a package for products that contain pharmaceutical active substances such as nicotine, fentanyl, or lidocaine.

In order to protect the aforesaid composite, made up of layers 12, 14, 16, and 18, from being undesirably opened or torn by curious children, who might thereby gain access to a packaged pharmaceutical active substance that is entirely unsuitable for children, a layer 22 made of biaxially oriented plastic, preferably of polyethylene terephthalate or polyamide, is laminated, by means of a layer 20 made of solvent-containing laminating adhesive at an application weight of 3 g/m², onto that side of aluminum layer 18 which faces away from COC layer 12.

Layer 22 can be imprinted on its side facing away from aluminum layer 18 product so that information regarding a product that is packaged using film composite 10 can be conveyed to a consumer. Layer 22 can then be an externally located layer, opposite from COC layer 12, of film composite 10.

Layer 22 can also be a paper layer rather than a plastic layer 22.

In the example depicted in FIG. 1 film composite 10 comprises, in addition to plastic layer 22, an externally located paper layer 26 joined by means of a further laminating-adhesive layer 24 made of solvent-containing laminating adhesive.

Paper layer 26 can be imprinted on its outward-facing exposed surface 26a. The imprint can be covered by a protective layer, for example clear lacquer.

In the example depicted, plastic layer 22 has a thickness of approximately 22.7 to 23.3 µm. Paper layer 26, on the other hand, has a thickness of approximately 39.5 to 40.5 µm at a weight per unit area of approximately 40 g/m².

The total thickness of film composite 10 is thus between 108.4 µm and 110.6 µm.

Film composite 10 not only has outstanding barrier properties with respect to migration and diffusion of pharmaceutical active substances or constituents thereof from outer surface 12a of COC layer 12 to outer surface 26a of paper layer 26. The rigidity of film composite 10 is furthermore very suitable for constitution of a package, and it has outstanding running properties on processing machines for processing film composite 10.

Figure 2:
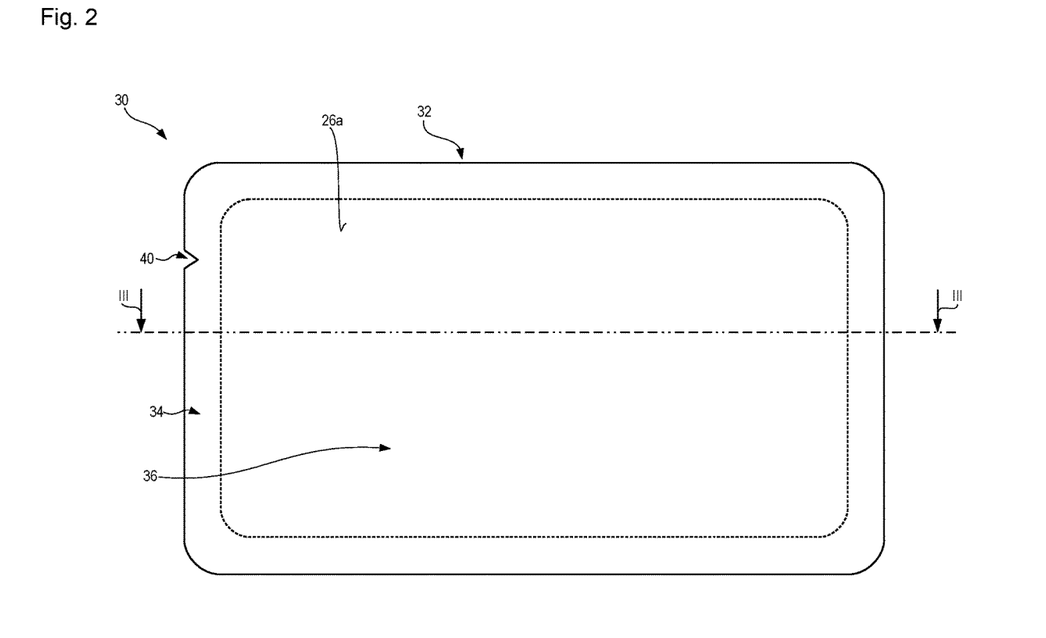
FIG. 2 is a plan view of a package, constituted with participation of the film composite of FIG. 1, of a transdermal patch.

FIG. 2 is a plan view of a package 30 constituted from two film-composite sheets of film composite 10 of FIG. 1, for packaging planar carriers of pharmaceutical active substances. Because of the plan view, only one film-composite sheet 32 is visible. A further film-composite sheet 33 is located behind film-composite sheet 32 depicted in FIG. 2 and is concealed by it (see FIG. 3). The viewer of FIG. 2 is looking onto outer side 26a of paper layer 26 of film-composite sheet 32. A "film-composite sheet" is understood for purposes of the present Application to mean any predetermined piece cut out of a film composite, regardless of the manner of cutting. The cut-out piece can therefore also be stamped or the like.

Package 30 is configured in the form of a four-side-sealed pouch having a surrounding sealed seam 34. Located radially inside sealed seam 34 is a carrier receiving space 36 in which a planar carrier 38 of a pharmaceutical active substance (see FIG. 3) is received.

Package 30 can comprise a notch 40 at at least one point, for example in an edge region, for easier opening.

Figure 3:
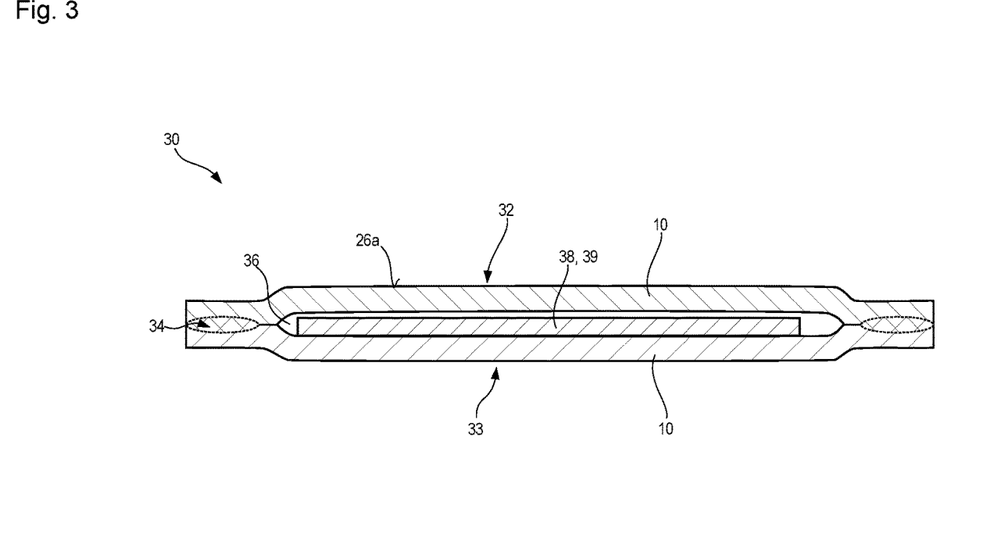
FIG. 3 is a cross-sectional view of the package of FIG. 2 along section plane III-Ill of FIG. 2.

FIG. 3 is a longitudinal section through package 30 of FIG. 2 along section plane III-III of FIG. 2. Section plane III-III is oriented orthogonally to the drawing plane of FIG. 2.

The distribution of layers within film-composite sheets 32 and 33 is no longer depicted separately in FIG. 3 in the longitudinal section through sheets 32 and 33. That distribution corresponds to the layer distribution of film composite 10 as depicted in FIG. 1. The two COC layers 12 of the respective film-composite sheets 32 and 33 are arranged facing toward one another and are fused to one another along sealed seam 34. A transdermal patch 39, constituting a planar carrier 38 of a pharmaceutical active substance, is received in carrier receiving space 36 that is constituted radially inside sealed seam 34. Carrier receiving space 36 is thus radially externally delimited by sealed seam 34 and orthogonally thereto by the two film-composite sheets 32 and 33.

Sealed seam 34 extends, in a thickness direction of the respective film-composite sheets 32 and 33, not only through the respective COC layers 12 that also serve as sealing layers but also, beyond those COC layers 12, into polyethylene layers 14. Sealed seam 34 is thus constituted by COC layers 12 (which are in contact with one another before sealing) of the two film-composite sheets 32 and 33 and by material of polyethylene layers 14 which are located, from the viewpoint of the contact point of the two COC layers 12 before sealed seam 34 is produced, behind the respective COC layers 12. Because the material of COC layers 12, like the material of polyethylene layers 14, is an olefin, the materials of the two layers 12 and 14 are mutually compatible and can blend with one another in sealed seam 34.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. A film composite for manufacturing a package for planar carriers of pharmaceutical active substances, comprising, in a direction from the outer side of the film composite toward its inner side:
   (i) a metal layer;
   (ii) an acrylic acid-containing joining layer;
   (iii) a polyethylene layer; and, (iv) a COC layer made of cycloolefin copolymer, a side of the COC layer which faces away from the metal layer being an exposed surface of the film composite, wherein the polyethylene layer comprises metallocene polyethylene to tie the COC layer to the acrylic acid-containing joining layer and thereby to the metal layer to promote the delamination stability of the film composite.

2. The film composite according to claim 1, wherein the proportion of metallocene polyethylene in terms of the total polyethylene of the polyethylene layer is at least 50 wt %.

3. The film composite according to claim 1, wherein the polyethylene layer comprises a metallocene linear low density polyethylene.

4. The film composite according to claim 1, wherein the polyethylene layer comprises at least one of a C6 metallocene polyethylene and a C8 metallocene polyethylene.

5. A film composite for manufacturing a package for planar carriers of pharmaceutical active substances, comprising, in a direction from the outer side of the film composite toward its inner side:
(i) a metal layer;
(ii) an acrylic acid-containing joining layer;
(iii) a polyethylene layer; and,
(iv) a COC layer made of cycloolefin copolymer, a side of the COC layer which faces away from the metal layer being an exposed surface of the film composite, wherein the polyethylene layer comprises a C8 metallocene linear low density polyethylene and wherein the polyethylene layer connects the COC-layer to the acrylic acid-containing joining layer and thereby to the metal layer to promote the delamination stability of the film composite.

6. The film composite according to claim 5, wherein the acrylic acid-containing joining layer is an ethylene-acrylic acid (EAA) copolymer.

7. The film composite according to claim 1, wherein each of the acrylic acid-containing joining layer, the polyethylene layer, and the COC layer, has a layer thickness in the range from about 7 μm to about 15 μm.

8. The film composite according to claim 7, wherein the thickness values of said layers, referred to the thinnest of said layers, differ by no more than 15%.

9. The film composite according to claim 8, wherein the thickness values of said layers, referred to the thinnest of said layers, differ by no more than 11%.

10. The film composite according to claim 7, wherein each of the layers, from among the acrylic acid-containing joining layer, the polyethylene layer, and the COC layer, has a layer thickness in the range from approximately 9 μm to 12 μm.

11. The film composite according to claim 10, wherein the thickness values of said layers, referred to the thinnest of said layers, differ by no more than 15%.

12. The film composite according to claim 11, wherein the thickness values of said layers, referred to the thinnest of said layers, differ by no more than 11%.

13. The film composite according to claim 1, wherein the film composite comprises, on the side of the metal layer which faces away from the COC layer, at least one further layer made of at least one of a paper and a plastic.

14. The film composite according to claim 13, wherein the at least one further layer includes a paper layer and a plastic layer.

15. The film composite according to claim 14, wherein the plastic layer is located closer to the metal layer than the paper layer.

16. The film composite according to claim 13, wherein the at least one further layer includes a plastic layer that is a biaxially oriented plastic.

17. The film composite according to claim 13, wherein the at least one further layer includes a plastic layer that is at least one of a polyethylene terephthalate and a polyimide.

18. The film composite according to claim 13, wherein the at least one further layer includes at least one of
(i) a paper layer having at least one of a thickness of 35 to 45 μm and a weight per unit area of 35 to 45 g/m$^2$ and
(ii) a plastic layer having at least one of a thickness of 19 to 27 μm and a weight per unit area of 28 to 36 g/m$^2$.

19. The film composite according to claim 18, wherein the at least one further layer includes at least one of
(i) a paper layer having at least one of a thickness of 39 to 41 μm and a weight per unit area of 39 to 41 g/m$^2$ and
(ii) a plastic layer having a thickness of 22 to 24 μm and a weight per unit area of 31 to 33 g/m$^2$.

20. A film composite for manufacturing a package for planar carriers of pharmaceutical active substances, comprising, in a direction from the outer side of the film composite toward its inner side:
(i) a metal layer;
(ii) an acrylic acid-containing joining layer;
(iii) a polyethylene layer; and
(iv) a COC layer made of cycloolefin copolymer,
wherein the polyethylene layer comprises metallocene polyethylene to tie the COC layer to the acrylic acid-containing joining layer and thereby to the metal layer to promote the delamination stability of the film composite, and wherein
each of the layers, from among the acrylic acid-containing joining layer, the polyethylene layer, and the COC layer, has a layer thickness in the range from about 7 μm to about 15 μm, and wherein
the thickness values of said layers, referred to the thinnest of said layers, differ by no more than 15%.

21. A film composite for manufacturing a package for planar carriers of pharmaceutical active substances, comprising, in a direction from the outer side of the film composite toward its inner side:
(i) a layer made of at least one of a paper and a plastic;
(ii) a metal layer;
(iii) an acrylic acid-containing joining layer;
(iv) a polyethylene layer; and,
(v) a COC layer made of cycloolefin copolymer, a side of the COC layer which faces away from the metal layer being an exposed surface of the film composite,
wherein the polyethylene layer comprises metallocene polyethylene to tie the COC layer to the acrylic acid-containing joining layer and thereby to the metal layer to promote the delamination stability of the film composite, and wherein
each of the layers, from among the acrylic acid-containing joining layer, the polyethylene layer, and the COC layer, has a layer thickness in the range from about 7 μm to about 15 μm, and wherein
the thickness values of said layers, referred to the thinnest of said layers, differ by no more than 15%.

22. The film composite according to claim 21, wherein the at least one further layer includes a paper layer and a plastic layer.

23. The film composite according to claim 22, wherein the plastic layer is located closer to the metal layer than the paper layer.

24. The film composite according to claim 23, wherein the at least one further layer includes a plastic layer that is a biaxially oriented plastic.

25. The film composite according to claim 24, wherein the at least one further layer includes a plastic layer that is at least one of a polyethylene terephthalate and a polyimide.

26. The film composite according to claim 21, wherein the at least one further layer includes at least one of
   (i) a paper layer having at least one of
      a. a thickness of 35 to 45 µm and
      b. a weight per unit area of 35 to 45 $g/m^2$ and
   (ii) a plastic layer having at least one of
      a. a thickness of 19 to 27 µm and
      b. a weight per unit area of 28 to 36 $g/m^2$.

27. A package for a planar carrier of pharmaceutical active substances, comprising two film-composite sheets of claim 1, wherein the two film-composite sheets are arranged with mutually facing COC layers to form a carrier receiving space and wherein the two film-composite sheets are joined to one another by local sealing of regions of the COC layers.

28. The package according to claim 27, wherein the package is a four-side-sealed pouch having a sealed seam surrounding the carrier receiving space.

29. The package according to claim 28, having a planar active-substance carrier, in particular a transdermal patch, contained in the carrier receiving space, the pharmaceutical active substance containing at least one of nicotine, fentanyl and lidocaine.

* * * * *

UNITED STATES PATENT AND TRADEMARK OFFICE
CERTIFICATE OF CORRECTION

| | |
|---|---|
| PATENT NO. | : 11,504,954 B2 |
| APPLICATION NO. | : 16/516792 |
| DATED | : November 22, 2022 |
| INVENTOR(S) | : Manuella Herb et al. |

It is certified that error appears in the above-identified patent and that said Letters Patent is hereby corrected as shown below:

In the Claims

Column 10, Line 6, Claim 17, the word "polyimide" should be replaced with --polyamide--.

Column 11, Line 6, Claim 25, the word "polyimide" should be replaced with --polyamide--.

Signed and Sealed this
Twenty-eighth Day of March, 2023

Katherine Kelly Vidal
*Director of the United States Patent and Trademark Office*